(12) United States Patent
Kofoed et al.

(10) Patent No.: US 6,312,389 B1
(45) Date of Patent: *Nov. 6, 2001

(54) MULTIPLE FUNCTION AIRWAY ADAPTER

(75) Inventors: Scott A. Kofoed; Joseph A. Orr, both of Salt Lake City, UT (US); David R. Rich, Glastonbury, CT (US)

(73) Assignee: NTC Technology, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/092,260

(22) Filed: Jun. 5, 1998

Related U.S. Application Data (63) Continuation of application No. 08/680,492, filed on Jul. 15, 1996, now Pat. No. 5,789,660.

(51) Int. Cl.$^7$ .......................................................... A61B 5/00
(52) U.S. Cl. ........................................... 600/532; 600/538
(58) Field of Search ...................................... 600/529, 534, 600/538, 532; 73/23.3

(56) References Cited

U.S. PATENT DOCUMENTS

| | | |
|---|---|---|
| 2,484,217 | 10/1949 | Gardenier . |
| 2,706,409 | 4/1955 | Preston . |

(List continued on next page.)

FOREIGN PATENT DOCUMENTS

| | | |
|---|---|---|
| 196 17 738 C1 | 6/1997 | (DE) . |
| 699939 | 11/1953 | (GB) . |
| 2052074 | 1/1981 | (GB) . |
| 2032118 | 4/1981 | (GB) . |
| 1509744 | 9/1989 | (RU) . |

OTHER PUBLICATIONS

*Flow Measurement*, 1991, pp. 124, 125, 474, 475, 477, 500, 558.

Miller, R.W., *Flow Measurement Engineering Handbook*, 1983, 9 pages.

Miller, R.W., *Flow Measurement Engineering Handbook*, 1989, 16 pages (unnumbered).

Ower, E., et al., "The Characteristics of Pitot and Status Tubes in Incompressible Flow," *The Measurement of Air Flow*, 1966.

"Basics of Auto Referencing," Sen. Sym., pp. 7–9 through 7–35, undated.

"Capnostat II CO2 Sensor," $CO^2$ *SMO User's Manual*, p. 16, Apr. 27, 1993.

Datex Brochure, "See Compliance at a Glance," undated.

Orr, et al., "A Respiratory Flowmeter Based on a Modified Mainstream $CO_2$ Cuvette," *Abstract presented at the Annual Meeting of the Society for Technology in Anesthesia*, 3 pages (unnumbered, Feb. 17–19, New Orleans, LA.

Rader, Con., "Pneumotachography," The Perkin Elmer Corporation, California Society of Cardiopulmonary Technologies Conference, Oct. 1982.

Saklad, Meyer, et al., "Pneumotachography: A New, Low–Dead Space, Humidity–Independent Device," *Anesthesiology*, vol. 5, No. 2, Aug. 1979, pp. 149–153.

Sullivan, William J., et al., "Pneumotachography: Theory and Clinical Application," *Respiratory Care*, vol. 29, No. 7, Jul. 1984, pp. 736–749.

*Primary Examiner*—Robert L. Nasser
(74) *Attorney, Agent, or Firm*—TrasBritt, P.C.

(57) ABSTRACT

An intergrated airway adapter capable of monitoring $CO_2$ concentration in real time, breath by breath, using infrared absorption techniques and monitoring respiratory flow with differential pressure flowmeters under diverse inlet conditions through improved sensor configurations which minimize phase tag and dead space within the airway adapter.

26 Claims, 9 Drawing Sheets

U.S. PATENT DOCUMENTS

| | | |
|---|---|---|
| 3,410,264 | 11/1968 | Frederik . |
| 3,449,954 | 6/1969 | Brown . |
| 3,581,565 | 6/1971 | Dieterich . |
| 3,590,473 | 7/1971 | Carlson . |
| 3,635,756 | 1/1972 | Shepard et al. . |
| 3,663,833 | 5/1972 | Pao et al. . |
| 3,726,271 | 4/1973 | Mondshine et al. . |
| 3,752,171 | 8/1973 | Ayre . |
| 3,889,536 | 6/1975 | Sylvester . |
| 3,910,113 | 10/1975 | Brown . |
| 3,937,082 | 2/1976 | Schilling . |
| 3,981,193 | 9/1976 | Goulet . |
| 4,036,054 | 7/1977 | Goulet . |
| 4,047,521 | 9/1977 | Kramer et al. . |
| 4,083,245 | 4/1978 | Osborn . |
| 4,154,100 | 5/1979 | Harbaugh et al. . |
| 4,163,390 | 8/1979 | Rodder . |
| 4,170,134 | 10/1979 | Nathan . |
| 4,345,463 | 8/1982 | Wilson et al. . |
| 4,346,584 | 8/1982 | Boebringer . |
| 4,372,170 | 2/1983 | Dehart et al. . |
| 4,403,514 | 9/1983 | Osborn . |
| 4,476,707 | 10/1984 | Burns et al. . |
| 4,481,829 | 11/1984 | Shortridge . |
| 4,546,655 | 10/1985 | Victor . |
| 4,581,942 | 4/1986 | Ogura et al. . |
| 4,581,945 | 4/1986 | Rusz . |
| 4,823,615 | 4/1989 | Taha . |
| 4,859,858 | 8/1989 | Knodle et al. . |
| 4,859,859 | 8/1989 | Knodle et al. . |
| 4,914,720 | 4/1990 | Knodle et al. . |
| 4,920,808 | 5/1990 | Sommer . |
| 4,957,007 | 9/1990 | Gray . |
| 4,958,075 | 9/1990 | Mace et al. . |
| 4,989,456 | 2/1991 | Stupecky . |
| 5,026,255 | 6/1991 | Carpenter et al. . |
| 5,038,773 | 8/1991 | Norlien et al. . |
| 5,088,332 | 2/1992 | Merlainen et al. . |
| 5,111,827 | 5/1992 | Rantala . |
| 5,137,026 | 8/1992 | Waterson et al. . |
| 5,153,436 | 10/1992 | Apperson et al. . |
| 5,251,121 | 10/1993 | Knodle et al. . |
| 5,347,843 | 9/1994 | Orr et al. . |
| 5,379,650 | 1/1995 | Kofoed et al. . |
| 5,443,075 | 8/1995 | Holscher . |
| 5,503,151 | 4/1996 | Harnoncourt et al. . |
| 5,535,633 | 7/1996 | Kofoed et al. . |
| 5,763,792 * | 6/1998 | Kullik .................................. 600/538 |

* cited by examiner

MULTIPLE FUNCTION AIRWAY ADAPTER

CROSS REFERENCE TO RELATED APPLICATION

This application is a continuation of application Ser. No. 08/680,492, filed Jul. 15, 1996, now U.S. Pat. No. 5,789,660, issued Aug. 4, 1998.

BACKGROUND OF THE INVENTION

1. Field of the Invention

The present invention relates to an airway adapter which monitors both airway $CO_2$ concentration and respiratory flow. More specifically, the present invention relates to an integrated airway adapter which is capable of monitoring $CO_2$ concentration in real time, breath by breath, using infrared absorption techniques in combination with monitoring respiratory flow with differential pressure flowmeters under diverse inlet conditions through improved sensor configurations.

2. State of the Art

U.S. Pat. Nos. 4,859,858 ("the '858 patent") and 4,859,859 ("the '859 patent"), issued Aug., 22, 1989 to Knodle et al.; and U.S. Pat. No. 5,153,436 ("the '436 patent"), issued Oct. 6, 1992 to Apperson et al., each disclose apparatus including analyzers for outputting a signal indicative of the concentration of a designated gas in a sample being monitored by each apparatus.

The gas analyzers disclosed in the '858, '859, and '436 patents are of the non-dispersive type. They operate on the principle that the concentration of a designated gas can be measured by passing a beam of infrared radiation through the gas and ascertaining the attenuated level of the energy in a narrow band absorbable by the designated gas. This process is accomplished using a detector capable of generating a concentration proportional electrical output signal.

One important application of gas analyzers is monitoring the level of carbon dioxide in the breath of a medical patient. This is typically done during a surgical procedure as an indication to the anesthesiologist of the patient's condition. Of course, such gas analyzers can also be used by doctors in numerous medical procedures, such as heart stress tests with a patient on a treadmill, and the like.

In a typical instrument using non-dispersive infrared radiation to measure gas concentration, infrared radiation is emitted from a source and focused into a beam by a mirror. The beam is transmitted through a sample of the gases being analyzed. After passing through the gases, the infrared radiation beam passes through a filter. The filter reflects all of the radiation except for the radiation in a narrow band which corresponds to a frequency absorbed by the gas of interest. This narrow band of radiation is transmitted to a detector which produces an electrical output signal proportional in magnitude to the magnitude of the infrared radiation impinging upon it. Thus, the radiation in the band passed by the filter is attenuated to an extent which is proportional to the concentration of the gas of interest. The strength of the signal generated by the detector is consequently inversely proportional to the concentration of the gas of interest.

In typical medical gas analyzers, a cuvette is used to sample a patient's gas exchange via a nasal cannula or by being placed between an endotracheal tube and the mechanical ventilator. The cuvette channels respirated gases to a specific flow path and provides an optical path between an infrared radiation emitter and an infrared radiation detector, both of which can be detachably coupled to the cuvette.

A typical cuvette is molded from a polymer or other appropriate material and has a passage defining the flow path for the gases being monitored. The optical path crosses the flow path of the gases through windows in the sidewalls of the cuvette aligned along opposite sides of the flow passage allowing the beam of infrared radiation to pass through the cuvette.

The windows are generally formed from sapphire because of sapphire's favorable optical properties. However, sapphire is a relatively expensive material. Consequently, these cuvettes are almost invariably cleaned, sterilized, and reused. The cleaning and sterilization of a cuvette is time-consuming and inconvenient, and the reuse of a cuvette may pose a significant risk of contamination, especially if the cuvette was previously used in monitoring a patient suffering from a contagious and/or infectious disease.

Efforts have been made to reduce the cost of cuvettes by replacing the sapphire windows with windows fabricated from a variety of polymers. One of the major problems encountered in replacing sapphire cuvette windows with polymer windows is establishing and maintaining a precise optical path through the sample being analyzed. This is attributable to such factors as a lack of dimensional stability in the polymeric material, the inability to eliminate wrinkles in the windows, and the lack of a system for retaining the windows at precise locations along the optical path.

U.S. application Ser. No. 08/300,146, hereby incorporated herein by reference, discloses a cuvette and a method of manufacturing same which eliminates the problems encountered in previous attempts to use polymers in the place of sapphire windows. The application discloses fashioning a window from a malleable homopolymer such as biaxially oriented polypropylene in the thickness range of 0.001 to 0.005 inches. The use of this inexpensive polypropylene material allows for the fabrication of single use, disposable cuvettes.

Respiratory flow measurement during the administration of anesthesia in intensive care environments and in monitoring the physical condition of athletes and other individuals prior to and during the course of training programs and medical tests provides valuable information for assessment of pulmonary function and breathing circuit integrity. Many different technologies have been applied to create a flowmeter that meets the requirements of the critical care environment. Among the flow measurement approaches which have been used are:

1) Differential Pressure—measuring the pressure drop or differential across a resistance to flow.
2) Spinning Vane—counting the revolutions of a vane placed in the flow path.
3) Hot Wire Anemometer—measuring the cooling of a heated wire due to airflow passing around the wire.
4) Ultrasonic Doppler—measuring the frequency shift of an ultrasonic beam as it passes through the flowing gas.
5) Vortex Shedding—counting the number of vortices that are shed as the gas flows past a strut placed in the flow stream.
6) Time of Flight—measuring the arrival time of an impulse of sound or heat created upstream to a sensor placed downstream.

Each of the foregoing approaches has various advantages and disadvantages, and an excellent discussion of most of these aforementioned devices may be found in W. J. Sullivan; G. M. Peters; P. L. Enright, M. D. "Pneumotachographs: Theory and Clinical Application," Respiratory Care, Jul. 1984, Vol. 29–7, pp. 736–49, and in C. Rader, Pneumotachography, a report for the Perkin-Elmer Corporation presented at the California Society of Cardiopulmonary Technologists Conference, October 1982.

At the present time, the most commonly used device for respiratory flow measurement is the differential pressure flowmeter. The relationship between flow and the pressure drop across a restriction or other resistance to flow is dependent upon the design of the resistance; thus many different resistance configurations have been proposed. The goal of many of these configurations is to achieve a linear relationship between flow and pressure differential.

In some prior art differential pressure flowmeters (commonly termed "pneumotachs"), the flow restriction has been designed to create a linear relationship between flow and differential pressure. Such designs include the Fleisch pneumotach in which the restriction is comprised of many small tubes or a fine screen, ensuring laminar flow and a linear response to flow. Another physical configuration is a flow restriction having an orifice variable in relation to the flow. This arrangement has the effect of creating a high resistance at low flows and a low resistance at high flows. Among other disadvantages, the Fleisch pneumotach is susceptible to performance impairment from moisture and mucous, and the variable orifice flowmeter is subject to material fatigue and manufacturing variabilities.

Most all known prior art differential pressure flow sensors suffer deficiencies when exposed to less than ideal gas flow inlet conditions, and further possess inherent design problems with respect to their ability to sense differential pressure in a meaningful, accurate, repeatable manner over a substantial dynamic flow range, particularly, when it is required for the flow sensor to reliably and accurately measure low flow rates, such as the respiratory flow rates of infants.

U.S. Pat. No. 5,379,650, issued Jan. 10, 1995 to Kofoed et al., hereby incorporated herein by reference, has overcome the vast majority of the problems with differential pressure flow sensors with a unique sensor including a tubular housing containing a diametrically-oriented, longitudinally extending strut containing first and second lumens having longitudinally-spaced pressure ports opening into respective axially-located notches at each end of the strut.

Developments in patient monitoring over the past several decades have shown that concurrent measurements of exhaled gas flow rate and $CO_2$ concentration provides information that is useful in therapy decision making. By combining these two measurement, one can calculate $CO_2$ production ($\dot{V}_{CO2}$) which is related to the patient's metabolic status. Also, these measurements can provide a graphical representation of the expired $CO_2$ concentration versus expired volume which provides information about gas exchange in different compartments of the lungs.

Presently, the apparatus necessary to acquire the combination of these two signals requires two discrete components: a flow sensor (pneumotach) and a $CO_2$ sensor. This configuration is cumbersome and adds undesirable volume (dead space) and resistance to the patient's breathing circuit.

It would be highly desirable to have an airway adapter which combines both a $CO_2$ concentration monitoring sensor and a respiratory flow monitoring sensor in a configuration which is convenient to use and which minimnizes phase lag and internal dead space of the combination.

SUMMARY OF THE INVENTION

The present invention comprises an integrated airway adapter for monitoring $CO_2$ concentration in real time, breath by breath, using infrared absorption techniques and monitoring respiratory flow with differential pressure flowmeters under diverse inlet conditions through improved sensor configurations.

The airway adapter of the present invention has been devoloped to address the issues of adapter size and phase lag performance. The present invention combines the functions of the $CO_2$ concentration monitoring adapter with that of the pneumotach into a single component. Two pressure ports (on the airway adapter) provide access such that a differential pressure is generated across the orifice of the pneumotach.

The airway adapter of the present invention is preferably manufactured by an injection molding process. The consistency of product obtainable from the injection molding process provides a high degree of interchangeability, thereby eliminating the need for a calibration procedure to be performed during setup or with disposable adapter replacement.

The airway adapter comprises a $CO_2$ concentration monitoring portion and respiratory flow sensor portion. The $CO_2$ concentration monitoring portion includes a chamber having a pair of opposing, axially aligned windows flanking the flow path, wherein the windows preferably have a high transmittance for radiation in the intermediate infrared portion of the electromagnetic spectrum. The axial alignment of the windows allows an infrared radiation beam to travel from an infrared radiation emitter transversely through the chamber and the gas(es) flowing through the chamber to an infrared radiation detector to determine the concentration of $CO_2$ in the gas.

The airway adapter can be either reusable or disposable. However, if the airway adapter is designed to be disposable, the windows should be made of an inexpensive material rather than sapphire as presently used. It is essential to the accuracy of the $CO_2$ monitoring sensor that the material used for the window transmit a usable part of the infrared radiation impinging upon it. Thus, the window material must have appropriate optical properties. A preferred window material is biaxially oriented polypropylene.

The respiratory flow sensor portion of the present invention has the capability of accommodating a wide variety of gas flow inlet conditions without adding significant system volume or excessive resistance to flow. The design of the respiratory flow sensor of the present invention also substantially inhibits the entrance of liquids in the monitoring system into the pressure ports of the sensor.

In a first embodiment, the respiratory flow sensor portion comprises a substantially tubular housing with a diametrically-onrented, longitudinally-extending strut having pressure ports located adjacent the axis of the housing and proximate each end of the strut. The pressure ports are each associated with a lumen contained within the strut, the lumens extending to the exterior of the sensor for communication via suitable tubing with a differential pressure transducer. Depending upon the flow direction being measured, one port serves as a high pressure tap and the other as a low pressure tap. The pressure ports are oriented substantially perpendicular to the axis of the tubular housing and communicate with the interior volume of the housing via axially-placed notches in the leading and trailing edges of the strut. It is preferred that the notches extend over the entire width of the strut in the area of the pressure ports and through the side faces of the strut so that the pressure ports have reduced response to the velocity of mass flow through the sensor.

In this preferred embodiment, the respiratory sensor portion is positioned between the mechanical ventilator and the $CO_2$ concentration monitoring portion.

In a second embodiment, the $CO_2$ concentration monitoring portion is designed to be detachable from the respiratory flow sensor portion. This embodiment is particularly useful for the cleaning and sterilization of a non-disposable airway adapter.

In a third embodiment, the exterior of a tubular portion of the $CO_2$ concentration monitoring portion is provided with external circumferential ribs, preferably defining a 22 mm diameter. The ribs reduce the adapter weight while providing uniform wall dimensions that assist molding of the part.

In a fourth and a fifth embodiment, the pressure ports are located on opposite sides of the $CO_2$ monitoring portion of the sensor. A first port is placed on the proximal (nearer to the patient) side, and the second port is placed on the distal (farther from the patient) side of the $CO_2$ monitoring portion of the sensor. This embodiment is particularly advantageous for use in situations where the respiratory tidal volumes are extremely small. This embodiment reduces the volume of expired gases which are rebreathed by the patient. Also, this embodiment uses the pressure perturbation and pressure loss of the $CO_2$ portion of the sensor as part of the flow signal. This reduces the overall pressure loss of the combined adapter. Though this embodiment is particularly advantageous for use with newborn infants, it also has equal utility in adult respiratory monitoring.

The respiratory flow sensor has a flow resistance element (whether the strut or the $CO_2$ concentration monitoring portion) which results in a differential pressure signal which is non-linear. To obtain adequate precision at extremely high and low flow rates, a very high resolution 18-bit or 20-bit analog to digital conversion device may be used. The use of such a converter allows a digital processor to compute flow from the measured differential pressure by using a sensor characterizing look-up table. This technique eliminates the need for variable or multiple gain amplifiers and variable offset circuits that might otherwise be required with use of a 12-bit resolution or lower resolution converter.

The airway adapter preferably incorporates a specific instrument connection scheme and is color or optically coded to prevent incorrect assembly. The airway adapter is to be manufactured in both permanent and disposable configurations.

BRIEF DESCRIPTION OF THE DRAWINGS

13 17.

DETAILED DESCRIPTION OF THE PREFERRED EMBODIMENTS

FIGS. 1–4 illustrate an airway adapter 20. The preferred airway adapter 20 is a unitary, injection-molded plastic element, so as to afford low manufacturing cost and permit disposal of the sensor after a single use, with a separate transducer housing 22 for housing an infrared emitter and an infrared absorption device which monitors $CO_2$ concentration. However, this configuration is not a requirement and the materials and method of fabrication are not critical to the invention. Suitable plastics include polycarbonates such as Lexan®, manufactured by General Electric, or Makrolon®, manufactured by Miles Chemicals.

The preferred airway adapter 20 is designed for connection between a patient ventilation device, such as an endotracheal tube inserted in a patient's trachea, attached to a first tubular portion 24 and the tubing of a mechanical ventilator attached at a second tubular portion 26. The first and second tubular portions 24 and 26 have bores of varying diameters and substantially circular cross-sections, with a $CO_2$ concentration monitoring portion 28 disposed therebetween. The second tubular portion 26 houses a respiratory flow monitoring device 30 therein.

Figure 1:
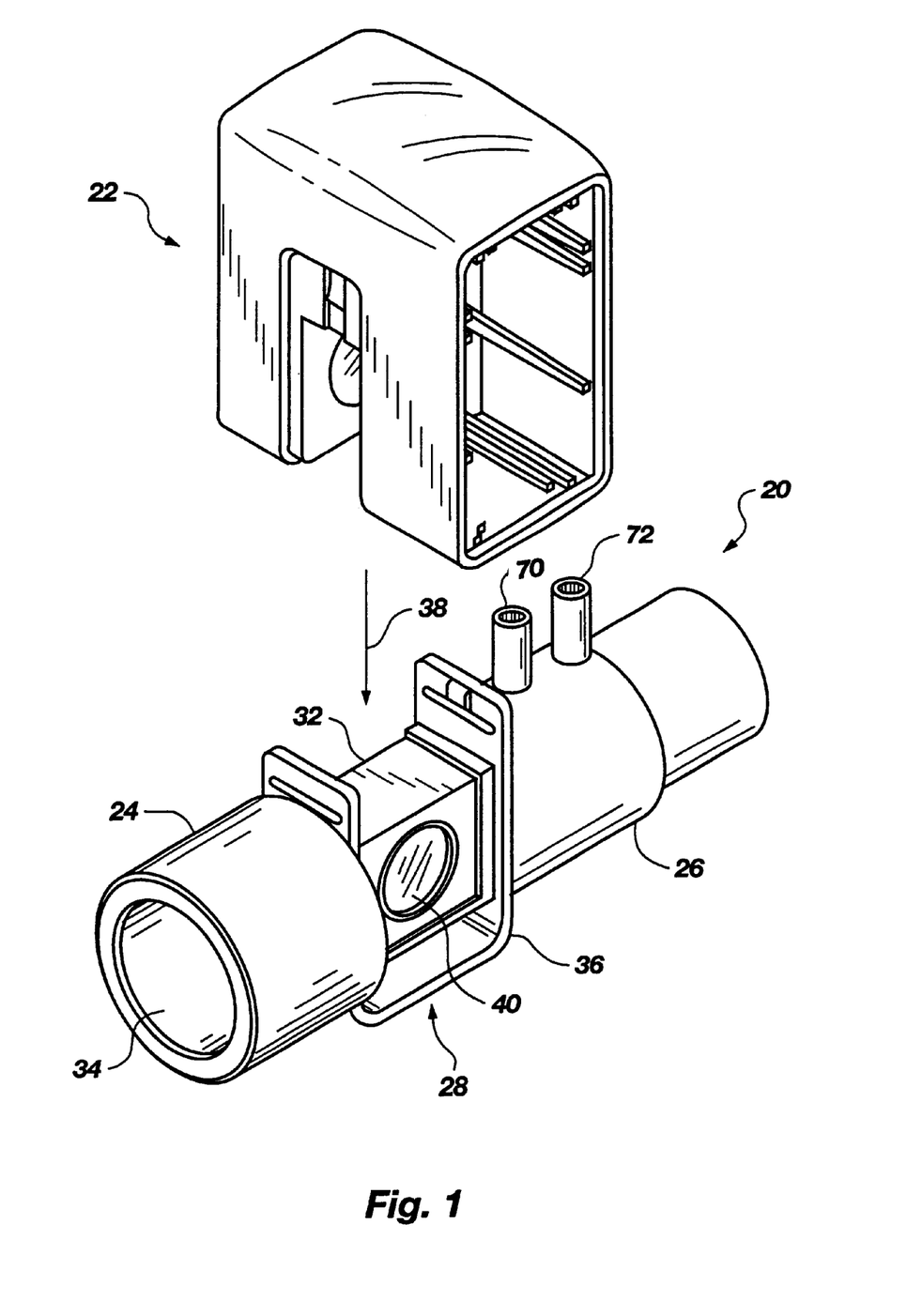
FIG. 1 is an exploded prospective view of a first preferred embodiment of the airway adapter of the present invention in combination with a transducer housing for containing electronics for $CO_2$ determination.

FIG. 1 illustrates the transducer housing 22 for electronics designed to output a signal proportional in magnitude to the concentration of carbon dioxide flowing through airway adapter 20, and a reference signal. These signals can be ratioed to provide a third signal accurately and dynamically representing the concentration of the carbon dioxide flowing through the airway adapter. The transducer housing 22 also includes an infrared radiation emitter (not shown). The internal configuration and design of the infrared absorption device housed in transducer housing 22 which monitors $CO_2$ concentration in real time is thoroughly discussed in U.S. application Ser. No. 08/300,383, previously incorporated by reference. It is understood that infrared $CO_2$ monitor devices such as those disclosed in the '858, '859, and '436 patents, as well as other $CO_2$ detection devices could be used in the transducer housing 22.

Figure 2:
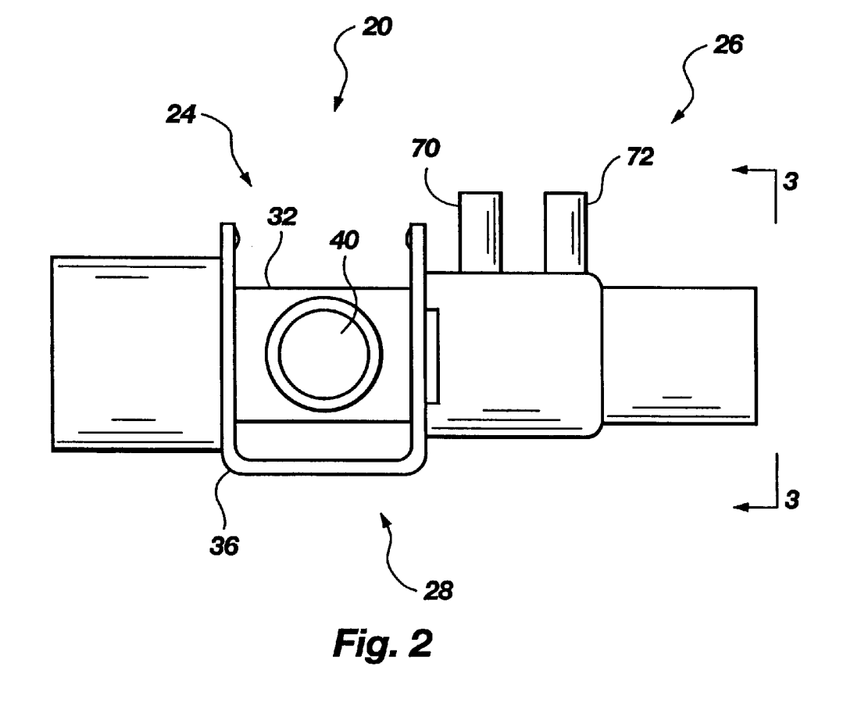
FIG. 2 is a side elevation view of a first preferred embodiment of the airway adapter of the present invention.
Figure 3:
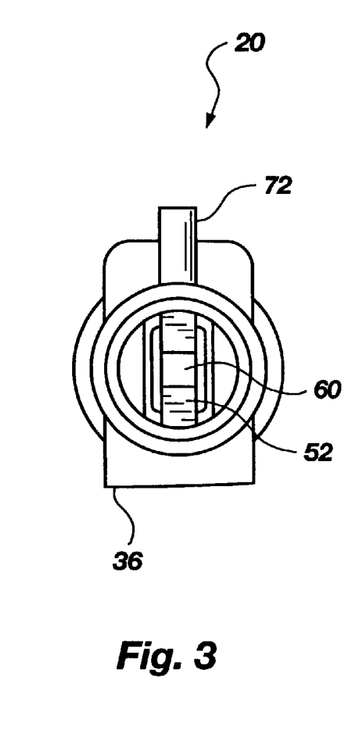
FIG. 3 is an end elevation view of the airway adapter of FIG. 2, looking from plane 3—3.

Referring more specifically to FIGS. 1–3, airway adapter 20 embodies the principles of the present invention and is typically molded from a polycarbonate or a comparable rigid, dimensionally stable polymer. The airway adapter 20 has a generally parallelepipedal center section 32 between and axially aligned with the first and second tubular portions 24 and 26 with a flow passage 34 extending from end-to-end through the airway adapter.

The $CO_2$ concentration monitoring portion 28 of airway adapter 20 provides a seat for transducer housing 22. An integral, U-shaped casing element 36 positively locates transducer housing 22 across the airway adapter 20 and, also, in the transverse direction indicated by arrow 38 in FIG. 1. The arrow 38 also shows the direction in which transducer housing 22 is displaced to detachably assemble it to the airway adapter 20. In a preferred embodiment, the airway adapter 20 snaps into place (see the above-cited '858 and '859 patents); no tools are needed to assemble or remove the adapter.

Figure 4:
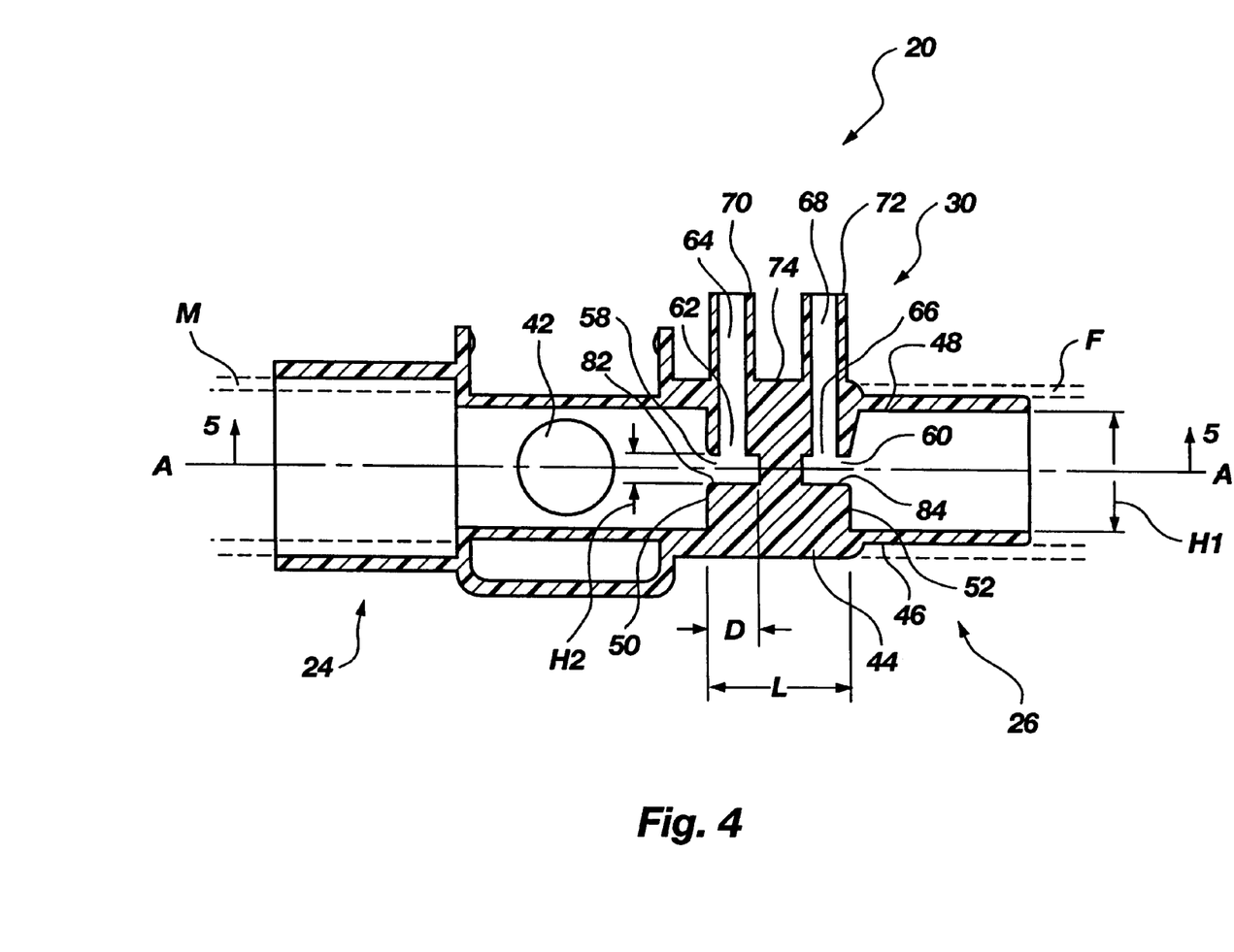
FIG. 4 is a side sectional elevation view of the airway adapter of FIG. 2.

The center section 32 includes first and second axially aligned windows 40 and 42, respectively (window 42 is shown only in FIG. 4). The windows 40 and 42 preferably have a high transmittance for radiation in the intermediate infrared portion of the electromagnetic spectrum. The axial alignment of first window 40 and second window 42 allows an infrared radiation beam to travel from the infrared radiation emitter in one leg of transducer housing 22 transversely through airway adapter 20 and the gas(es) flowing through airway adapter flow passage 34 to an infrared radiation detector (not shown) in the opposing, parallel leg of transducer housing 22.

Cuvette windows have typically been fabricated from sapphire because of sapphire's favorable optical properties; stability; and resistance to breakage, scratching, and other forms of damage. However, sapphire windows are expensive, and this makes it impractical to discard the cuvette after it is used to monitor a single patient. Instead, the cuvette must be cleaned, sterilized, and reused, which is inconvenient and poses a risk of infection to the patient.

In a preferred embodiment, the cost of the cuvette can be reduced to the point of making it practical to dispose of the cuvette after a single use by fabricating the cuvette windows from an appropriate polymer rather than the many times more expensive sapphire. It is essential to the accuracy of the $CO_2$ concentration monitor that the polymer transmit a usable part of the infrared radiation impinging upon it. Thus, the window material must have the appropriate optical properties. Such appropriate preperties may include a polymer that is malleable, of which a preferred window material is biaxially oriented polypropylene.

Figure 5:
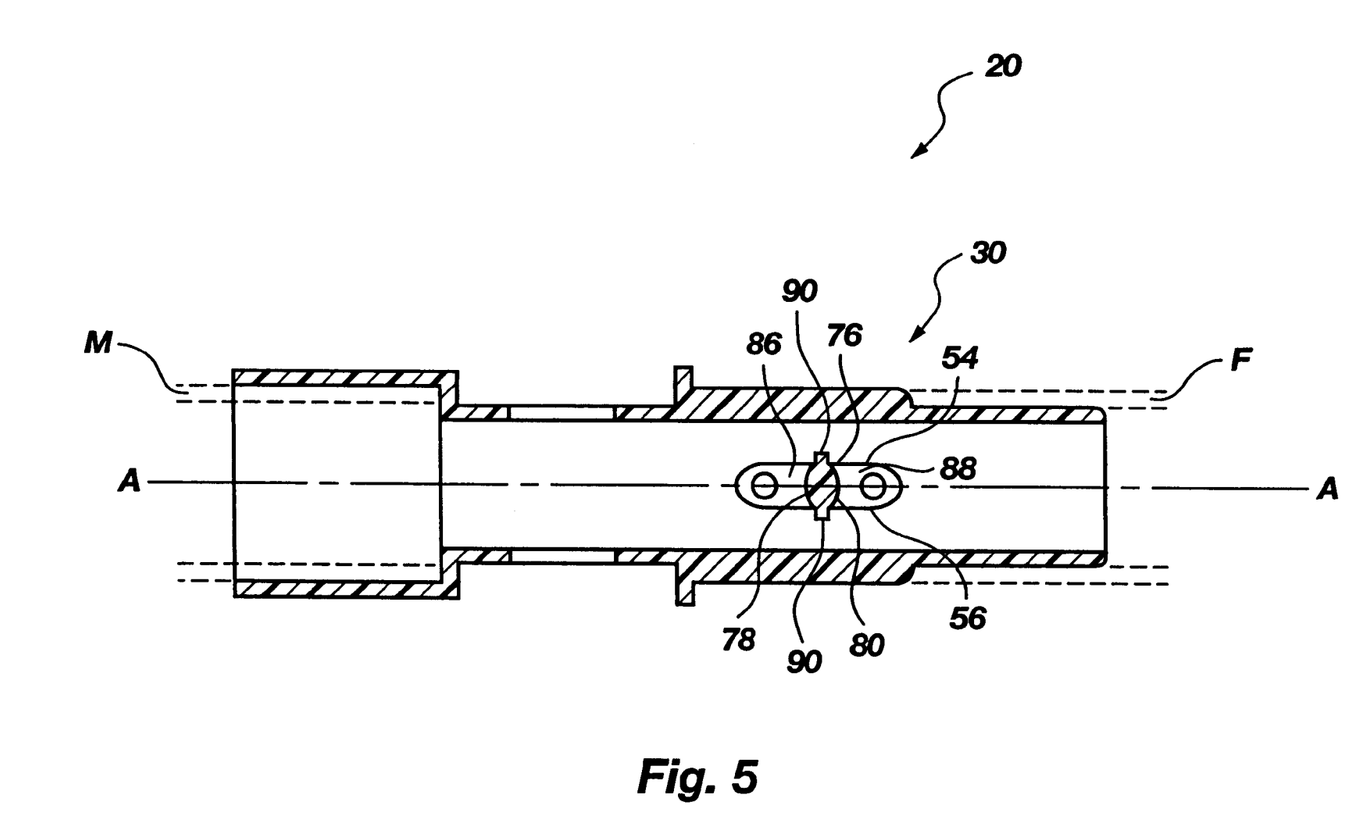
FIG. 5 is a secional view of the airway adapter of FIG. 4, looking upward from plane 5—5 extending laterally across the axis of the present invention.

As discussed above, airway adapter 20 includes the respratory flow monitoring device 30 within the first tubular portion 24 (most clearly seen in FIGS. 4 and 5). The respiratory flow monitoring device 30 includes a diametrically-oriented, longitudinally-extending strut 44 of axial length L and height H1. The strut 44, which provides a position for pressure ports apertures 62 and 66 and conditions the velocity profile of the flowing gas, offset from the inner wall 48 of the tubular housing 46, is secured at both ends to the inner wall 48 of the tubular housing 46, has first and second end faces 50 and 52, respectively, and has first and second side faces 54 and 56, respectively. The cross-sectional area of the strut 44 transverse to a bore axis A should be minimized. The minimization of this dimension is constrained by the diameter of the pressure ports 62 and 66. Typically this may be five percent (5%) of the cross-sectional bore area of the tubular housing 46 at the strut location.

It should be noted that the bore diameter of the tubular housing 46 depicted in FIGS. 4–5 is different between first portion 24 and second portion 26. This is intentional in the preferred embodiment to accommodate a male connecting tube element shown in broken lines and designated as M on the left-hand side or first portion 24 of the airway adapter 20, and a female connecting tube element F on the right-hand side or second portion 26 of the airway adapter 20. Also, the internal bores may be tapered to allow for mold release from a plastic injection molding machine.

The strut 44 further includes notch structures comprising substantially symmetrical first notch 58 and a second notch 60 located substantially on axis A of the tubular housing 46, notches 58 and 60 extending axially inwardly from first and second end faces 50 and 52, respectively, and laterally through first and second side faces 54 and 56, respectively. A first pressure port 62 of a first lumen 64 opens into the first notch 58, and a second pressure port 66 of a second lumen 68 opens into the second notch 60, first and second lumens 64 and 68 comprising passages internal to the strut 44 which extend into and through a first and second male stem 70 and 72, respectively, on the exterior surface 74 of the tubular housing 46. The respiratory flow monitoring device 30 is proportional to the square root the differential pressure as measured at the pressure ports 62 and 66.

Both pressure ports 62 and 66 face substantially perpendicular to axis A of tubular housing 46, and the notches 58 and 60 extend axially inwardly to a depth D at least past the pressure ports 62 and 66, and may so extend a distance equal to the height H2 of the notches 58 and 60, which in turn should be less than or equal to four-tenths (4/10) of the height H1 of the strut 44.

The back walls 78 and 80 of the notches 58 and 60, respectively, together with the restrictions (ridges or lands) 90 comprise an obstruction 76 and/or perturbation to the gas flow which generates the differential pressure signal which is measured at first and second pressure ports 62 and 66. The measured differential pressure signal is from either pressure loss or from vena contracta. Vena contracta is the contraction of the flowing gas velocity profile caused by the flow obstruction. The differential pressure generated from the vena contracta can be modeled by standard fluid mechanics equations such as Euler's or Bernoulli's equation. The differential pressure signal generated from vena contracta is considered "lossless", meaning that the pressure is restored as the velocity profile is returned to that incident to the sensor.

The flow obstruction 76 may be varied in a number of ways to yield a different magnitude of measured differential pressure for a given flow rate. First, the cross-sectional area of the restrictions (ridges or lands) 90 may be increased or decreased in the plane perpendicular to axis A. Also, the distance from the center of the first pressure port 62 to the back wall 78 of notch 58, and likewise the center of the second pressure port 66 to the back wall 80 of notch 60, may be varied to change the flow response characteristics. The magnitude of the differential pressure signal for a given flow rate can be further increased by reducing the cross-sectional bore area by necking down the inner wall of tubular housing 46.

The length and width of the strut may be altered as desired to change flow characteristics. These flow characteristics include flow conditioning, signal strength, and signal stability. Ideally the incident velocity profile to the obstruction should be the same regardless of the velocity profile incident to the airway adapter 20. Signal stability may be compromised when unstable multi-dimensional vortex formations are generated by the obstruction 76. The strut 44 with notch means provides flow conditioning that yields some immunity to inlet velocity profile and yields a stable differential pressure signal in response to the gas flow.

It is contemplated that the end faces 50 and 52 may be substantially perpendicular to axis A as shown in FIGS. 4 and 5, chamfered and rounded as shown, so long as the end face configuration is symmetrical when viewed from above. The major characteristic of the end faces 50 and 52, aside from symmetry, is that they do not incline toward notches 58 and 60 or otherwise collect or direct flow through the respiratory flow monitoring device 30 toward the notches 58 and 60 and the pressure ports 62 and 66. The end faces 50 and 52 are to be aerodynamically designed to minimize resistance to the gas flow.

Side faces 54 and 56 of strut 44 are flat as shown in FIGS. 4 and 5, again the major requirement as with the end faces 50 and 52 being one of symmetry between the sides of the strut 44.

Back walls 78 and 80 of the notches 58 and 60, respectively, are arcuate or radiused as shown in FIG. 5, or otherwise symmetrically shaped, as with the end faces 50 and 52. The back walls 78 and 80 may also be flat.

Floors 82 and 84 and ceilings 86 and 88 of the notches 58 and 60, respectively, are preferably flat as shown in FIGS. 4 and 5, or may be otherwise symmetrically shaped. Likewise, the transition edges or lines between the end faces 50 and 52 and the notches 58 and 60 are preferably radiused, although alternatively chamfered or bevelled.

The foregoing modifications of the respiratory flow monitoring device 30 of FIGS. 4 and 5 may be selectively employed to adapt to the conditions under which the sensor is to operate. In particular, the modification of the cross-sectional flow area in the vicinity of the strut 44 may be employed to adjust the dynamic range of the respiratory flow monitoring device 30, as may modifications of the configuration of the end faces, the back walls of the notches, and to the lines of transition between the notches and the end faces and side faces. It is preferred to use laterally extending, transversely oriented center (strut 44) restrictions (ridges or lands) 90 and a gradual inner wall transition in the strut area axial length to add symmetry to the flow pattern, normalize the flow, provide immunity to moisture, and provide better repeatability of readings. The notch height H2 or the length of the structure may be increased or decreased to accommodate a wider range of inlet conditions, such as might result from employment of the respiratory flow monitoring device 30 with a variety of endotracheal tubes.

The airway adapter 20 is preferably oriented with the first and second male stems 70 and 72 directed upward, such that the water condensation and mucous does not clog or otherwise impair the pressure ports 62 and 66.

Figure 6:
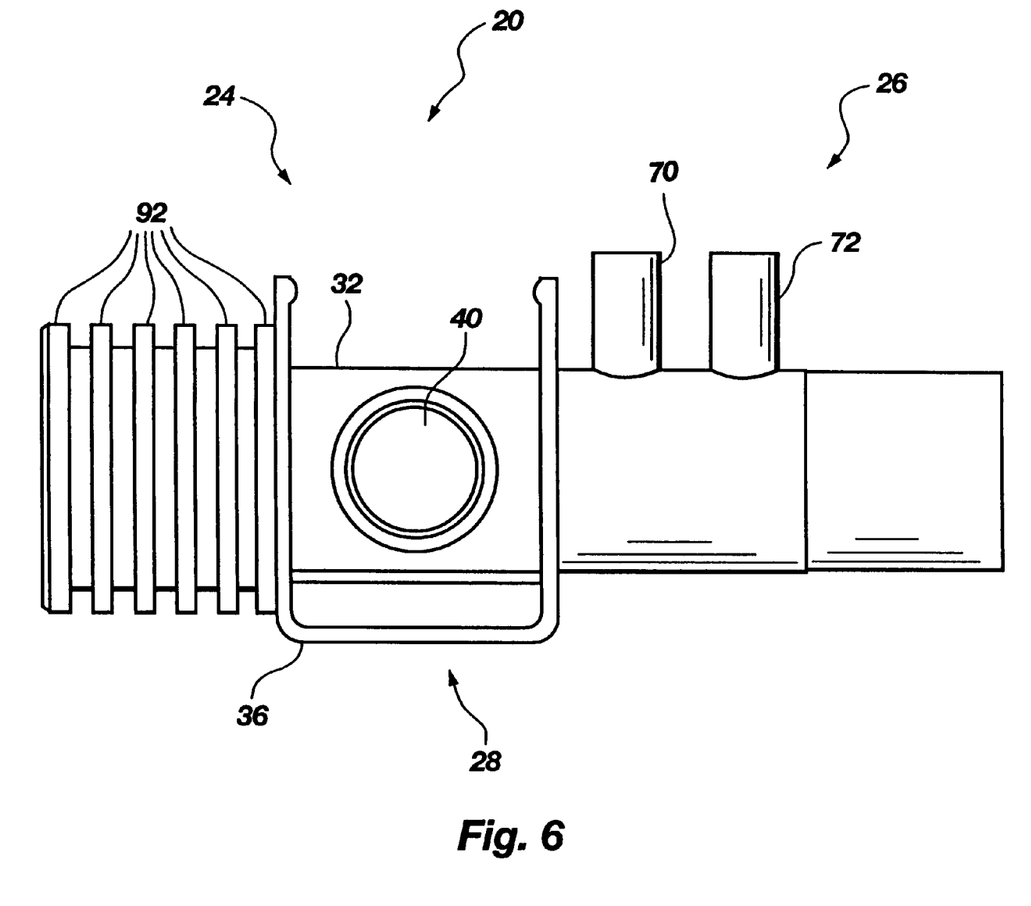
FIG. 6 is a side elevation view of a second preferred embodiment of the airway adapter of the present invention.

FIG. 6 illustrates a second embodiment of the airway adapter 20 which includes a plurality of ribs 92 around the outside diameter of the first tubular portion 24 of the airway adapter 20. The ribs preferably define a 22 mm diameter and reduce the adapter weight while providing uniform wall dimensions that assist molding of the part.

Figure 7:
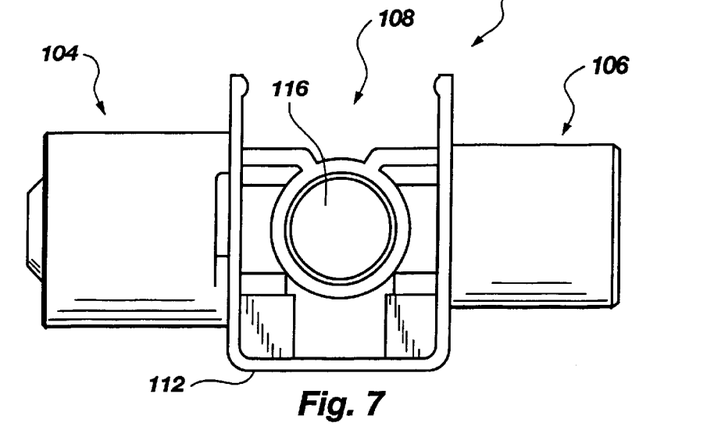
FIG. 7 is a side elevation view of a third preferred embodiment of the airway adapter of the present invention.
Figure 8:
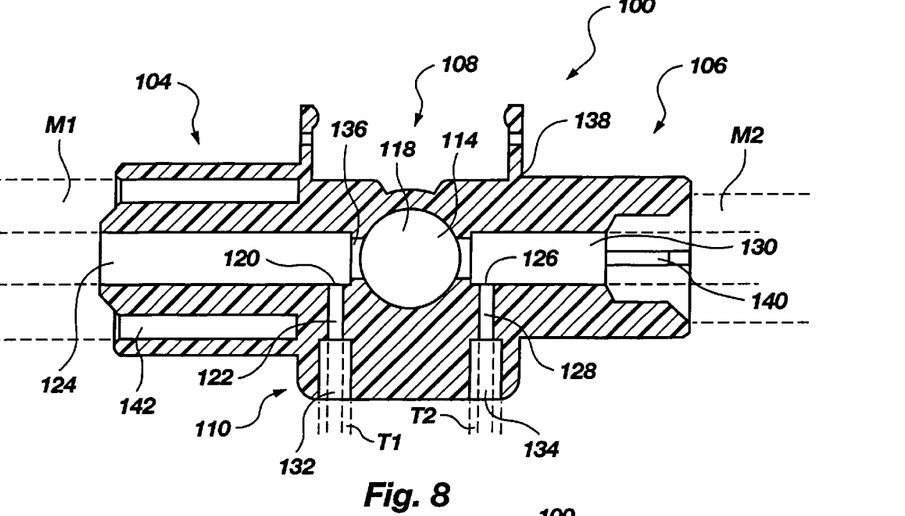
FIG. 8 is a side sectional elevation of the airway adapter of FIG. 7.
Figure 9:
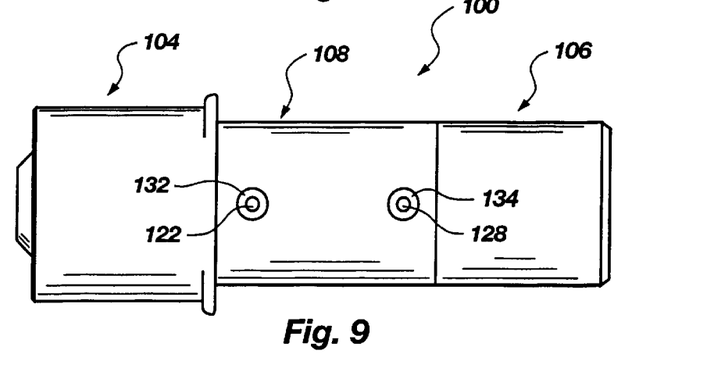
FIG. 9 is a bottom view of the airway adapter of FIG. 7.

FIGS. 7–9 illustrate a third embodiment of an airway adapter 100 which is particularly suitable for use in situations where the respiratory tidal volumes are extremely small, such as with newborn infants, although it has equal utility in adult respiratory monitoring.

The preferred airway adapter 100 is also designed for connection between a patient ventilation device, such as an endotracheal tube inserted in a patient's trachea, attached to a first tubular portion 104 and the tubing of a mechanical ventilator attached at a second tubular portion 106. The first and second tubular portions 104 and 106 have bores of varying diameter and of substantially circular cross-section, with a $CO_2$ concentration monitoring portion 108 disposed therebetween.

The $CO_2$ concentration monitoring portion 108 of the airway adapter 100 provides a seat for a ransducer housing (not shown), simila to the transducer housing 22 shown in FIG. 1. An integral, U-shaped casing element 112 positively locates the transducer housing into position. In a preferred embodiment, the airway adapter 100 snaps into place without the need for tools to assemble or remove the adapter.

The $CO_2$ monitoring portion 108 also includes a first axially aligned window 116 and a second axially aligned window 118 (shown in FIG. 8 only) to allow an infrared radiation beam to travel from the infrared radiation emitter in the transducer housing transversely through a sampling chamber 114 in adapter 100 for monitoring $CO_2$ gas as discussed above.

The airway adapter 100 includes a respiratory flow monitoring device 110 which partially resides in the first tubular portion 104, partially resides in the second tubular portion 106, and partially resides in the intermediate $CO_2$ monitoring portion 108. The respiratory flow monitoring device 110 is most clearly seen in FIG. 8. The respiratory flow monitoring device 110 comprises a first pressure port 120 of a first lumen 122 which opens into a first tubular chamber 124 of the first tubular portion 104, and a second pressure port 126 of a lumen 128 which opens into the second tubular chamber 130, lumens 122 and 128 extending to a first recess 132 and a second recess 134, respectively. The recesses 132 and 134 are configured to minimize dead space and accommodate male connecting tubes shown in broken lines and designated as T1 and T2. Tubes T1 and T2 are connected to a flow monitor (now shown) which determines flow rate through a pressure differential detected between the pressure ports 120 and 126. This pressure differential is produced through the use of necked-down ports 136 and 138 at the longitudinal ends of $CO_2$ sampling chamber 114.

In this embodiment, an annular recess 142 is formed in the first tubular portion 104 to accommodate a male connecting tube element shown in broken lines and designated as M1 on the left-hand side or first tubular portion 104 of the airway adapter 100. The second tubular portion 106 accommodates a second male connection be element M2, as shown in broken lines. The element M2 includes a bore of like diameter to the bore of second tubular chamber 130, and snaps into the second portion 106 by engaging a stepped slot 140.

It has been found that this embodiment has many advantages such as minimization of dead space and moldability in one piece. The sampling chamber 114 with ports 136 and 138 serves a dual function by adding a differential pressure flow signal to $CO_2$ measurement. The heat from the $CO_2$ transducer housing placed over the airway adapter 100 should help to reduce the tendency of breath moisture to condense in the airway adapter 100. The effects of water condensation are of particular concern in this embodiment due to its small volume and intended neonatal use; therefore the airway adapter 100 should be positioned such that recesses 132 and 134 are directed upward to prevent clogging.

FIGS. 10–17 illustrate a fourth preferred embodiment of an airway adapter 200 which is similar to the airway adapter 100 of FIGS. 7–9; therefore, components common to FIGS. 7–9 and FIGS. 10–17 retain the same numeric designation. The airway adapter 200 is also particularly suitable for use in situations where the respiratory tidal volumes are extremely small, such as with newborn infants, although it has equal utility in adult respiratory monitoring.

The preferred airway adapter 200 is also designed for connection between a patient ventilation device, such as an endotracheal tube inserted in a patient's trachea, attached to the first tubular portion 104 and the tubing of a mechanical ventilator attached at second tubular portion 106. The first and second tubular portions 104 and 106 have bores of varying diameter and of substantially circular cross-section, with the $CO_2$ concentration monitoring portion 108 disposed therebetween.

Figure 10:
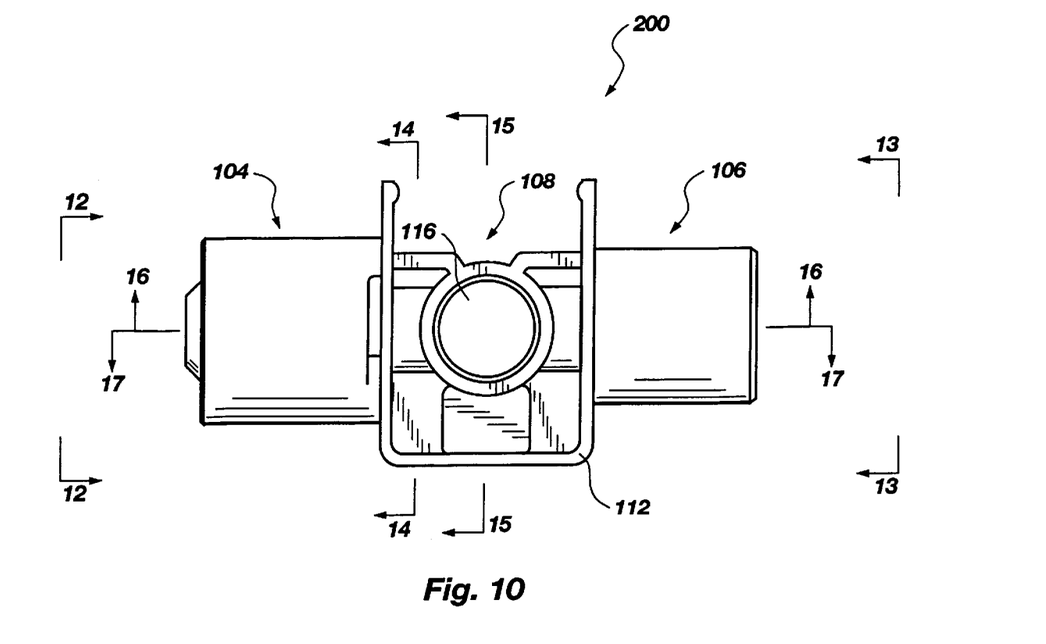
FIG. 10 is a side elevation view of a fourth preferred embodiment of the airway adapter of the present invention.

The $CO_2$ concentration monitoring portion 108 of the airway adapter 200 provides a seat for a transducer housing (not shown), similar to the transducer housing 22 shown in FIG. 1. An integral, U-shaped casing element 112 positively locates the transducer housing into position. In a preferred embodiment, the airway adapter 200 snaps into place without the need for tools to assemble or remove the adapter.

Figure 11:
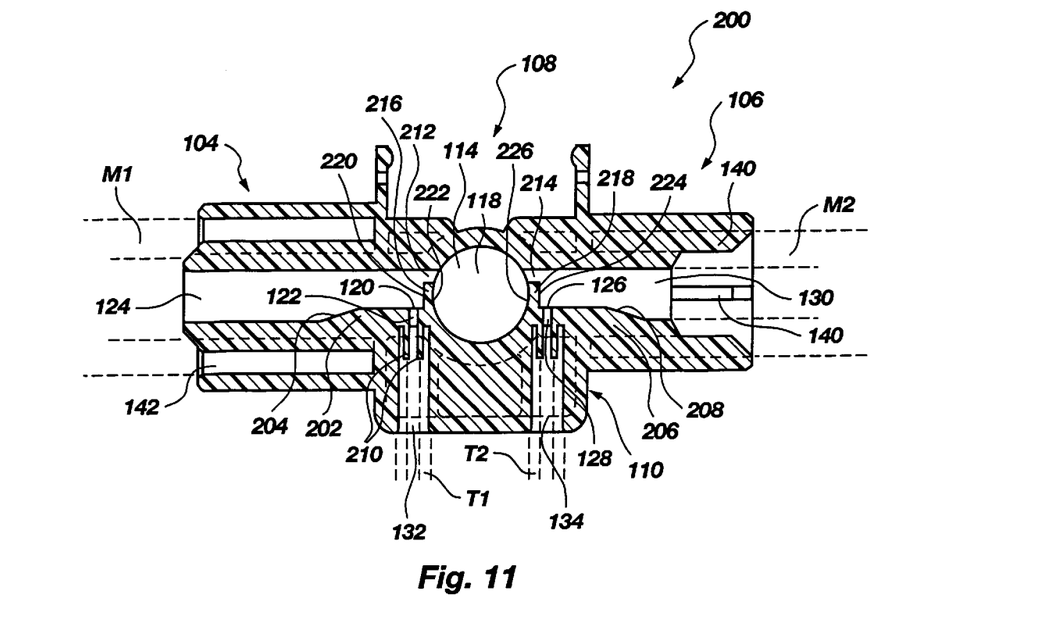
FIG. 11 is a side sectional elevation of the airway adapter of FIG. 10.
Figure 12:
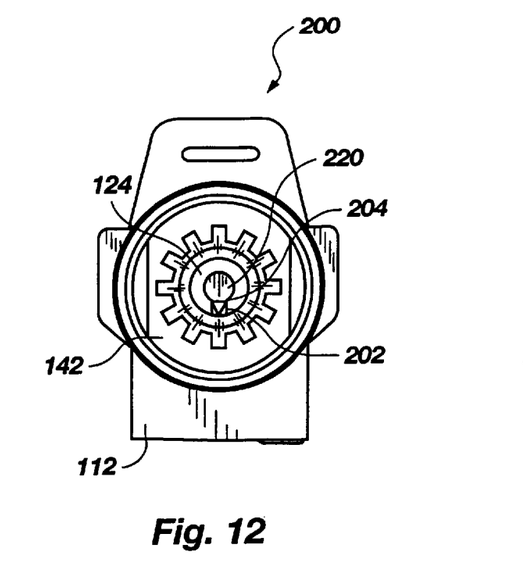
FIG. 12 is an end elevation view of the airway adapter along lines 12—12 of FIG. 10.
Figure 13:
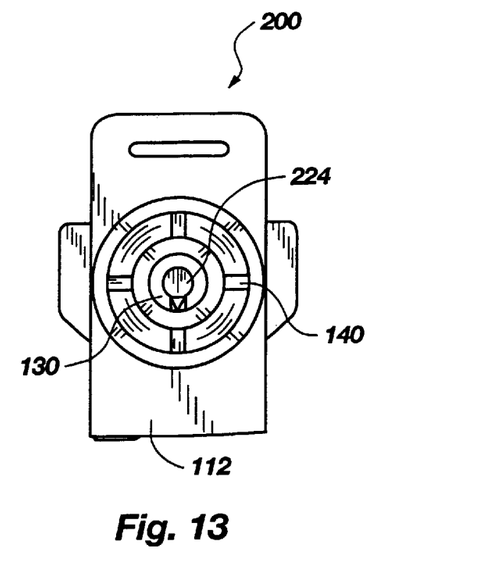
FIG. 13 is an end elevation view of the airway adapter along lines 13—13 of FIG. 10.
Figure 14:
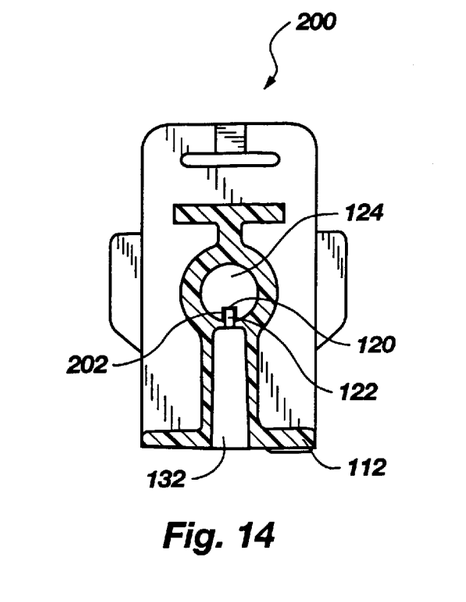
FIG. 14 is a sectional view of the airway adapter of FIG. 10, looking from plane 14—14.
Figure 15:
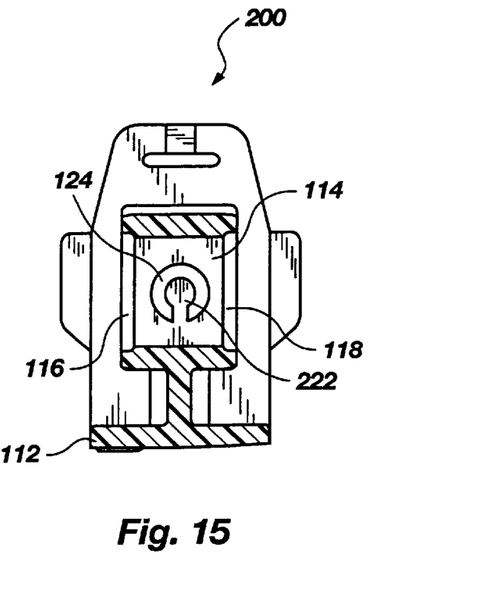
FIG. 15 is a sectional view of the airway adapter of FIG. 10, looking from plane 15—15.
Figure 16:
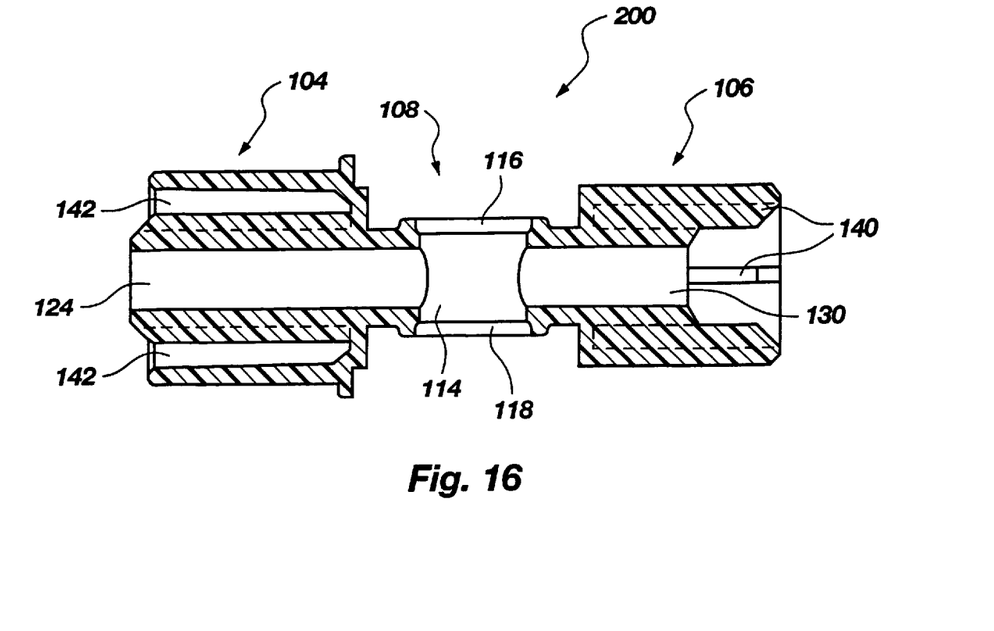
FIG. 16 is a sectional view of the airway adapter of FIG. 10, looking from plane 16—16.
Figure 17:
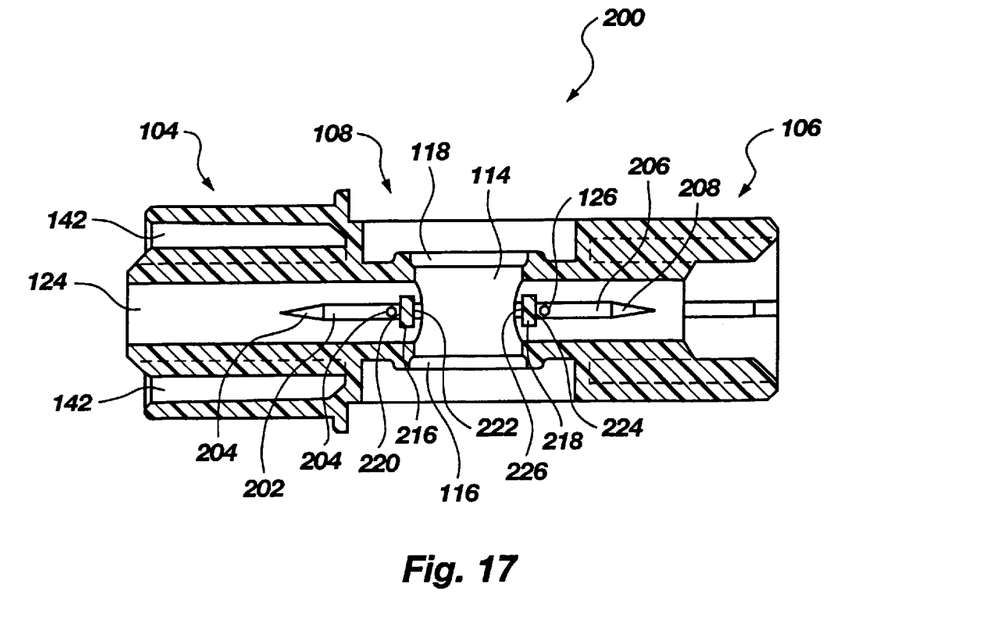
FIG. 17 is a sectional view of the airway adapter of FIG. 10, looking from plane 17

The $CO_2$ monitoring portion 108 also includes a first axially aligned window 116 and a second axially aligned window 118 to allow an infrared radiation beam to travel from the infrared radiation emitter in the transducer housing transversely through the sampling chamber 114 in the adapter 200 for monitoring $CO_2$ gas as discussed above.

The airway adapter 200 includes a respiratory flow monitoring device 110 which partially resides in the first tubular portion 104, partially resides in the second tubular portion 106, and partially resides in the intermediate $CO_2$ monitoring portion 108. The respiratory flow monitoring device 110 comprises the first pressure port 120 of a first lumen 122 which extends through a first strut 202 and opens into the first tubular chamber 124 of the first tubular portion 104. The first strut 202 has a tapered portion 204 directed toward the first tubular portion 104 to minimize potential flow disturbances. The respiratory flow monitoring device 110 further comprises the second pressure port 126 of a lumen 128 which extends through a second strut 206 and opens into the second tubular chamber 130. The second strut 206 has a tapered portion 208 directed toward the second tubular portion 106 to minimize potential flow disturbances. The lumens 122 and 128 extend to the first recess 132 and the second recess 134, respectively.

The recesses 132 and 134 are configured to minimize dead space and accommodate male connecting tubes shown in broken lines and designated as T1 and T2. The recesses 132 and 134 may have internal ribs 210 to securely grip the tubes T1 and T2. The tubes T1 and T2 are connected to a flow monitor (now shown) which determines flow rate through a pressure differential detected between the pressure ports 120 and 126. This pressure differential is produced through the use of a first annular port 212 and a second annular port 214 at the longitudinal ends of $CO_2$ sampling chamber 114. The first annular port 212 is formed by a first restriction member 216 extending from the first strut 202 and blocking a portion of the first tubular chamber 124 of first tubular portion 104. The face surfaces 220, 222 of the first restriction member 216 are preferably substantially perpendicular to the flow of the respiratory gas within the airway adaptor 200. The second annular port 214 is formed by a second restriction member 218 extending from the second strut 206 and blocking a portion of the second tubular chamber 130 of the second tubular portion 106. The face surfaces 224, 226 of the second restriction member 218 are preferably substantially perpendicular to the flow of the respiratory gas within the airway adaptor 200. The first restriction member 216 and the second restriction member 218 can be any shape such a circular, oval, rectangular, or the like. However, the preferred shape is a planar disk.

In this embodiment, as with the embodiment of FIGS. 7–9, an annular recess 142 is formed in the first tubular portion 104 to accommodate a male connecting tube element shown in broken lines and designated as Ml on the left-hand side or first tubular portion 104 of the airway adapter 200. Second tubular portion 106 accommodates the second male connecting tube element M2, as shown in broken lines. The element M2 includes a bore of like diameter to the bore of second tubular chamber 130, and snaps into second tubular portion 106 by engaging stepped slot 140.

It has been found that this embodiment has many advantages such as minimization of deadspace and moldability in one piece. The sampling chamber 114 with ports 212 and 214 serves a dual function by adding a differential pressure flow signal to $CO_2$ measurement. The heat from the $CO_2$ transducer housing placed over the airway adapter 200 should help to reduce the tendency of breath moisture to condense in adapter 200. The effects of water condensation are of particular concern in this embodiment due to its small volume and intended neonatal use; therefore, the airway adapter 200 should be positioned such that recesses 132 and 134 are directed upward to prevent clogging.

While the airway adapter of the present invention has been disclosed herein in terms of a preferred and alternative embodiment and modifications thereto, those of ordinary skill in the art will appreciate that many other additions, deletions and modifications to the disclosed embodiments may be effected without departing from the scope of the invention as hereinafter claimed.

What is claimed is:

1. An integrated airway adapter providing a $CO_2$ concentration monitoring capability and a differential pressure measurement capability for determining respiratory gas flow, said integrated airway adapter comprising:

a housing having a bore and a longitudinal axis;

a first pressure port and a second pressure port opening into said bore and structure communicating with said first pressure port and said second pressure port exterior to said housing for detecting a pressure differential in respiratory gas flowing through said housing bore;

a structure located within said housing bore for creating said pressure differential;

a detection chamber defined within said housing at least partially between said first pressure port and said second pressure port, said detection chamber communicating with said bore; and a pair of windows located on opposing sides of said detection chamber and aligned along an optical path traversing the detection chamber, each of said pair of windows being optically compatible to allow a beam of infrared radiation originating on one side of said detection chamber to traverse said respiratory gas when located in said detection chamber to be received by a detecting system to determine a $CO_2$ concentration in said respiratory gas.

2. The integrated airway adapter of claim 1, wherein said first and second pressure ports face substantially perpendicular to said longitudinal axis of said housing.

3. The integrated airway adapter of claim 1, wherein said pair of windows are fabricated from a segment of infrared radiation transmitting polymer.

4. The integrated airway adapter of claim 3, wherein said infrared radiation transmitting polymer is malleable.

5. The integrated airway adapter of claim 4, wherein said infrared radiation transmitting polymer is a biaxially oriented polypropylene.

6. The integrated airway adapter of claim 1, wherein said structure for creating said pressure differential comprises at least one strut with at least one of said first pressure port and second pressure port disposed therein.

7. The integrated airway adapter of claim 6, wherein said at least one strut has a restriction member disposed thereon which is oriented with a face surface substantially perpendicular to a direction of said respiratory gas flow.

8. The integrated airway adapter of claim 7, wherein said restriction member includes a planar disk shape member.

9. The integrated airway adapter of claim 6, wherein said at least one strut is tapered toward one end of said detection chamber.

10. The integrated airway adapter of claim 1, wherein said first pressure port is located proximate one end of said detection chamber and said second pressure port is located proximate another end of said detection chamber.

11. The integrated airway adapter of claim 10, wherein said structure for creating said pressure differential comprises a first strut proximate one end of said detection chamber with said first pressure port and a second strut proximate another end of said detection chamber with second pressure port disposed therein.

12. The integrated airway adapter of claim 11, wherein at least one of said first strut and said second strut has a restriction member disposed thereon which is oriented with a face surface substantially perpendicular to a direction of said respiratory gas flow through said housing bore.

13. The integrated airway adapter of claim 11, wherein at least one of said first strut and said second strut is tapered toward one end of said detection chamber.

14. The integrated airway adapter of claim 1, further comprising a strut diametrically disposed and longitudinally extending within said housing bore, said strut having a first end face, a second end face, a first side face, a second side face, an axial length along the longitudinal axis of said housing, and material affixed thereto to restrict said respiratory gas flow through said housing bore;

first and second longitudinally spaced notches in said strut located proximate said longitudinal axis of said housing for allowing said respiratory gas flow thereinto from said bore, said first notch extending from said first end face axially inward into said strut and from said first side face to said second side face, said second notch extending from said second end face axially inward into said strut and from said first side face to said second side face; and said first and second pressure ports respectively opening into said first and second notches from first and second lumens contained within said strut and extending to an exterior of said housing.

15. The integrated airway adapter of claim 14, wherein said first and second longitudinally spaced notches in said strut each include a curved back wall surface portion.

16. The integrated airway adapter of claim 15, wherein said first and second longitudinally spaced notches extend longitudinally into said strut at least as far as longitudinally innermost extents of said first and second pressure ports.

17. The integrated airway adapter of claim 14, wherein said first and second longitudinally spaced notches have heights perpendicular to said longitudinal axis of said housing less than or equal to about four-tenths of a height of said strut, taken in the same direction.

18. The integrated airway adapter of claim 14, wherein said strut has a cross-sectional area of at least about ten percent of that of the bore of said housing at a location of said strut.

19. The integrated airway adapter of claim 14, wherein said bore of said housing is constricted adjacent a bore wall proximate the location of a portion of said strut.

20. The integrated airway adapter of claim 19, wherein said constriction of said bore comprises a reduction in bore diameter proximate the location of a portion of said strut.

21. The integrated airway adapter of claim 14, wherein said housing bore proximate one longitudinal extent of said strut is greater in diameter than said housing bore proximate another longitudinal extent of said strut.

22. The integrated airway adapter of claim 14, wherein said strut includes first and second longitudinal ends oriented perpendicular to said longitudinal axis of said housing.

23. The integrated airway adapter of claim 22, wherein the first and second longitudinal ends of said strut are rounded.

24. The integrated airway adapter of claim 14, wherein said bore of said housing is constricted between said first and second pressure ports.

25. The integrated airway adapter of claim 24, wherein said constriction is provided by said material and comprises transversely orient lands extending laterally outwardly from said strut.

26. The integrated airway adapter of claim 1, wherein said structure for creating said pressure differential defines at least one boundary of said detection chamber.

* * * * *

UNITED STATES PATENT AND TRADEMARK OFFICE
CERTIFICATE OF CORRECTION

PATENT NO.    : 6,312,389 B1
DATED         : November 6, 2001
INVENTOR(S)   : Scott A. Kofoed, Joseph A. Orr and David R. Rich It is certified that error appears in the above-identified patent and that said Letters Patent is hereby corrected as shown below:

Title page,
Item [75], Inventors, change "Glastonbury" to -- Glastronbury --
Item [63], Related U.S. Application Data, after "5,789,660" insert -- , issued Aug. 4, 1998 --
Item [56], FOREIGN PATENT DOCUMENTS, change Document No. 1, "196 17 738 C1 6/1997 (DE)" to -- DE 196 17 738 C1 6/1997 (GE) -- and;
Document No. 2, change "GB" to -- (UK) -- and;
Document No. 3, change "GB" to -- (UK) -- and;
Document No. 4, change "4/1981 (GB)" to -- 4/1980 (UK) --
Item [56], OTHER PUBLICATIONS, Orr, et al., change "presented" to -- Presented -- and; "(unnumbered)" to -- (unnumbered) --
U.S. PATENT DOCUMENTS, change "Boebringer" to -- Boehringer -- and; change "Merlainen" to -- Merilainen --
Item [74], *Attorney, Agent, or Firm*, change "TrasBritt" to -- TraskBritt --
Item [57], ABSTRACT, change "intergrated" to -- integrated -- and; change "lag" to -- tag --

Column 2,
Line 5, after "passage" insert -- , --
Line 22, after "path" insert -- length --
Line 27, change "application" to -- Application --

Column 3,
Line 46, change "measurement," to -- measurements, --

Column 4,
Line 48, change "onrented" to -- oriented --

Column 6,
Lines 14 and 15, change "plane 17 13 17." to -- plane 17 - 17. --
Line 52, change "application" to -- Application --
Line 55, after "devices" insert -- , --
Line 64, after "adapter" insert -- 20 --

Column 7,
Line 39, change "preperties" to -- properties --
Line 43, change "respiratory" to -- respiratory --
Line 48, after "ports" delete "apertures"
Lines 61 and 62, after "first" insert -- tubular --
Lines 62 and 67, after "second" insert -- tubular --
Line 65, after "first" insert -- tubular --

UNITED STATES PATENT AND TRADEMARK OFFICE
CERTIFICATE OF CORRECTION

PATENT NO. : 6,312,389 B1
DATED : November 6, 2001
INVENTOR(S) : Scott A. Kofoed, Joseph A. Orr and David R. Rich It is certified that error appears in the above-identified patent and that said Letters Patent is hereby corrected as shown below:

Column 8,
Line 57, after "Ideally" insert -- , --

Column 9,
Line 67, change "ransducer" to -- transducer --

Column 10,
Line 1, change "simila" to -- similar --
Line 28, change "(now shown)" to -- (not shown) --
Line 38, change "connection be" to -- connecting tube --
Line 53, after "therefore" insert -- , --

Column 11,
Line 44, change "(now shown)" to -- (not shown) --
Line 63, after "such" change "a" to -- as --

Column 12,
Line 9, change "deadspace" to -- dead space --

Column 14,
Line 40, change "orient" to -- oriented --

Signed and Sealed this

Twenty-eighth Day of January, 2003

JAMES E. ROGAN
*Director of the United States Patent and Trademark Office*